United States Patent
Petty et al.

(10) Patent No.: US 6,877,724 B1
(45) Date of Patent: Apr. 12, 2005

(54) CONSTANT CONCENTRATION DELIVERY DEVICE AND METHOD FOR VAPORIZED SUBSTANCES

(75) Inventors: Jimmie D. Petty, Columbia, MO (US); Walter L. Cranor, Columbia, MO (US); James N. Huckins, Columbia, MO (US); David A. Alvarez, Columbia, MO (US); Gary Robertson, Henderson, NV (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 102 days.

(21) Appl. No.: 10/402,870

(22) Filed: Mar. 31, 2003

(51) Int. Cl.[7] ................................................. B01F 3/04
(52) U.S. Cl. ........................ 261/30; 261/78.2; 261/104; 261/DIG. 65; 427/69
(58) Field of Search ........................... 261/24, 30, 104, 261/78.2, DIG. 65; 427/69; 422/28

(56) References Cited

U.S. PATENT DOCUMENTS

| | | | |
|---|---|---|---|
| 947,726 A | 1/1910 | Zimmer | |
| 1,034,777 A | 8/1912 | Foster | |
| 1,528,640 A | 3/1925 | Tvrzicky et al. | |
| 2,614,820 A | 10/1952 | Boydjieff | 261/26 |
| 3,577,710 A | 5/1971 | Feldman | 55/316 |
| 4,208,902 A | 6/1980 | Kim et al. | 73/19 |
| 5,906,794 A * | 5/1999 | Childers | 422/28 |
| 6,030,436 A | 2/2000 | Barclay | 95/45 |
| 6,234,455 B1 | 5/2001 | Wittek | 261/30 |

* cited by examiner

Primary Examiner—Robert A. Hopkins
(74) Attorney, Agent, or Firm—Mark Homer

(57) ABSTRACT

A zero emmission device and method for delivering constant concentration of a vaporized substance allows for the regulated use of chemical or biological substances, such as calibrating, exposure or therapeutic substances.

19 Claims, 11 Drawing Sheets

6 A

6 B

CONSTANT CONCENTRATION DELIVERY DEVICE AND METHOD FOR VAPORIZED SUBSTANCES

STATEMENT REGARDING FEDERALLY SPONSORED RESEARCH OR DEVELOPMENT

Figure 1:
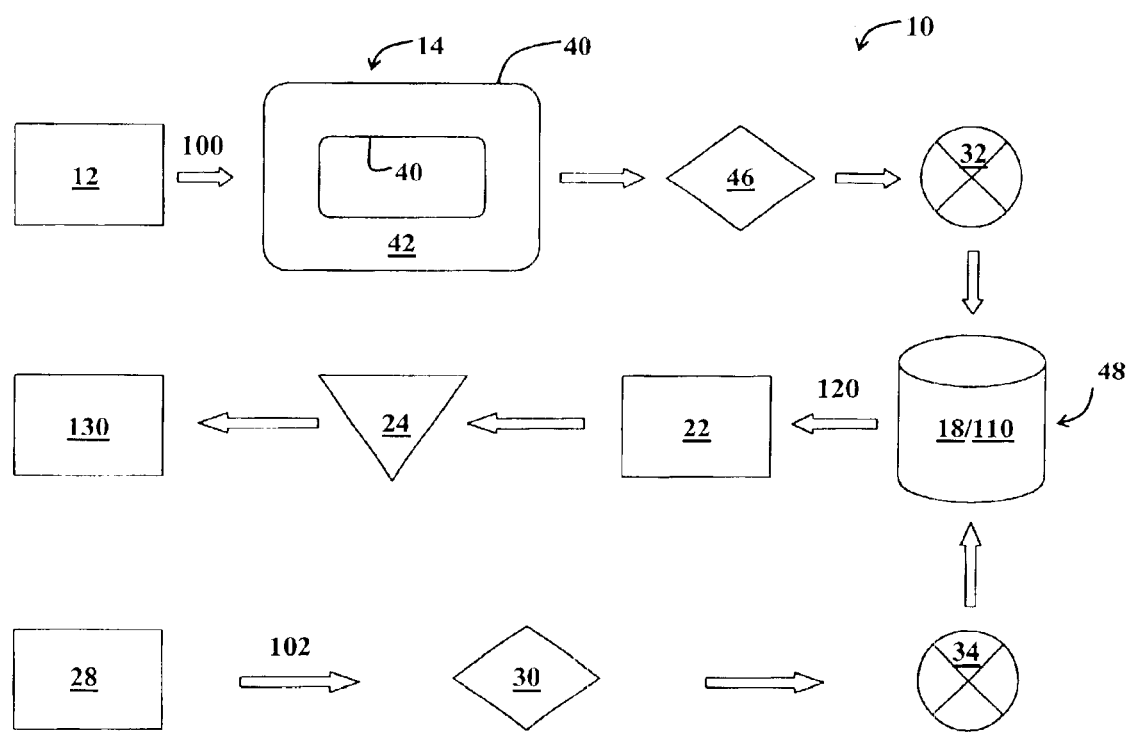

The invention described herein may be manufactured and used by or for the government of the United States of America for governmental purposes without the payment of any royalties thereon or therefore.

BACKGROUND OF THE INVENTION

1. Field of the Invention

A device for, method for, and product of, providing a constant concentration, preferably constant flow, chemically or biologically enhanced gas.

2. Brief Description of the Related Art

Emissions of vapor phase chemicals and their concomitant global transport in the atmosphere have increased orders of magnitude over the past 100 years due primarily to anthropogenic releases associated with industrial, agricultural, domestic, and recreational activity. Closely associated with the increases in emissions of complex mixtures to the atmosphere are the ubiquitous occurrences of such atmospheric contaminants in areas far removed from any direct input source. Fish and other aquatic organisms have been demonstrated to be highly efficient at bioconcentrating many of these atmospheric contaminants from water, resulting in serious health risk to consumers. In addition, food chains based on aquatic organisms can lead to contamination of birds and mammals. Vapor phase transport of contaminants throughout the global environment is of great concern due to increasing energy production, industrial activity, and intensive agricultural on a worldwide basis. Further, the majority of people spend most of their lives in indoor areas and are exposed to the complex mixture of airborne chemicals present in such areas. Exposures to indoor air contamination is increasingly being recognized as having the potential to result in detrimental effects, e.g., the so-called Asick building syndrome.@ Consequently, monitoring the presence of and determining the biological effects of vapor phase contaminants in the atmosphere has immediate importance and will become increasingly critical for the foreseeable future.

Many scientists, such as those at the Columbia Environmental Research Center (CERC), are charged with, as an integral part of their research mission, the development of methods for sampling and analysis of environmental contaminants. Laboratories conducting analytical and toxicological research concerning the presence and toxicity of vapor phase chemicals must have facilities that are designed to provide a constant concentration of the airborne chemical or mixtures of chemicals for exposure studies or for calibration of air sampling devices in the case of determining the presence of ambient levels of atmospheric chemical contaminants. To accomplish these tasks, researchers and engineers have devoted enormous effort and extensive resources to design and construct systems to safely produce constant concentrations of vapor phase chemicals.

Generally the production of airborne chemicals involves either aerosols, i.e., an assembly of liquid or solid particles suspended in a gaseous medium at a particle size in the range 0.001 to 100 $\mu$m or particulate matter (PM) in various sizes, e.g., PM 10, PM 100, etc. Specifically, aerosols are generated from pure liquids, suspensions, or dry powders employing nebulizers, vibrating orifice mondisperse aerosol generators, spinning disk monodisperse aerosol generators or dry powder dispersers (see e.g., Johnson, D. L., K. D. Carlson, T. A. Pearce, N. A., Esmen, B. N. Thomas. 1999. Effects of Nebulization Time and Pressure on Lipid Microtubule Suspension and Areosol, Aerosol Science and Technology, 30:211–222; Phillips, M. L., C. C. Meagher, D. L. Johnson. 2001. What is Powder-Free?: Characterization of Powder Aerosol Produced During Simulated Use of Powder-Free Latex Gloves, Occupational and Environmental Medicine, 58:479–481; and Clinkenbeard, R. E, D. L. Johnson, R. Parthasarathy, C. Altan, K. H. Tan, R. H. Crawford, S. M. Park. 2002. Replication of Human Tracheobronchial Hollow Airway Models Using a Selective Laser Sintering Rapid Prototyping Technique, American Industrial Hygiene Association Journal, 63:141–150.). All these systems for producing airborne suspensions of chemicals and particulate matter involve relatively complex mechanical apparatus. Other than through the manipulation of temperature, few examples of systems for producing vapor phase chemicals soluble in the gaseous medium as individual molecules exist. These systems generally rely on some form of generator apparatus, e.g., a column of glass beads coated with pure chemical through which the gaseous medium passes, a multi compartment apparatus for generation of vapor phase chemicals in which in one or more compartments pure chemical is present and the gaseous medium is used to carry the vapor to subsequent compartments, etc. Both the inherent complexity of the mechanical apparatus and the variable physicochemical parameters of the test chemicals impede the use of any of these systems for studying complex mixtures of airborne chemicals.

Control of the production of the vapor phase chemicals in the currently used systems depends, in general, on mechanical manipulations, e.g., nebulizers, varying the temperature, saturating the gaseous medium with aerosol/particles, etc. There is a distinct lack of precedence for the controlled production of airborne mixtures using polymeric membrane diffusion of chemicals.

Although some non-ionic organic compounds are known to diffuse through synthetic nonporous polymers (see e.g., Comyn, J., Ed., Polymer Permeability, Elsevier Applied Science Publishers LTD: New York, N.Y., 1985.), use of these polymers as a control mechanism for generating vapor phase mixtures of organic chemicals is lacking. In addition, this type of system is unknown as a method to produce and deliver constant concentrations of complex mixtures of vapor phase organic chemicals for calibration of air samplers or for organism exposures. Current methods for generating vapor phase chemicals generally are designed to be used with single chemicals or very limited chemical mixtures and often result in the generation of aerosols rather than true vapor phase mixtures of chemicals.

Accordingly, there is a need in the art to provide a vapor phase mixture of chemicals or biologicals for administration, calibration and testing. The present invention addresses this and other needs.

SUMMARY OF THE INVENTION

The present invention includes a device for delivering constant concentrations of a vaporized substance comprising a chamber having walls defining an enclosed recyclable area, a gaseous medium inlet located through the walls of the chamber capable of sealing the interior of the chamber from the exterior of the chamber in the absence of allowing gas to flow into the chamber, a circulating component communicatively aligned with the interior of the chamber capable of circulating the gas within the recyclable area, a substance reservoir communicatively accessed to the interior of the recyclable area for imparting a vaporized substance into the gas within the recyclable area and a substance enhanced gaseous medium outlet from the recyclable area capable of sealing the interior of the chamber from the exterior of the chamber in the absence of allowing the substance enhanced gas to flow out of the chamber.

The present invention also includes a process for delivering a constant concentration of a vaporized substance comprising steps of providing the preciously described device and moving gas through the gaseous medium inlet into the interior of the recyclable area, circulating the moved gas within the recyclable area sufficient to recycle the gas within the recyclable area, continuously imparting vaporized substance into the circulating and recycled gas wherein the concentration of the vaporized substance within the gas progress to a steady state to create a substance enhanced gas and passing the substance enhanced gas from the interior of the recyclable area through the substance enhanced gaseous medium outlet. A constant concentration vaporized substance product is delivered by the process herein, with the product preferably including either a calibrating or therapeutic substance.

The present invention provides a means of producing and delivering, in a reproducible and highly precise manner, biologically relevant mixtures of airborne organic chemicals. In addition, the device of the present invention is applicable for reducing and/or removing vapor phase organic chemicals from buildings or other contamination sites of limited area using a constant flow of the polluted air and the integrative sequestration of vapor phase chemicals through the technology described herein. Such applications can be combined with high efficiency filters to reduce vapor phase chemicals and particulate matter. Furthermore, the device of the present invention can be employed to conduct exposure assessment of humans and direct exposure of organisms (e.g., wildlife, birds, etc.) to complex mixtures of biologically available mixtures of vapor phase chemicals. Producing constant concentrations of vapor phase chemicals uses the controlled volatilization of individual chemicals within the mixture, with the added complexity of sampling complex mixtures of vapor phase neutral molecules using nonporous polymeric films. This is particularly based on easily decontaminated materials and controlled volatilization employing membrane permeation and atmospheric diffusion processes.

BRIEF DESCRIPTION OF THE DRAWINGS

FIG. 1 illustrates a block diagram of the multi-component system of the present invention;

FIG. 2 illustrates a core element of the present invention;

FIG. 3 illustrates an internal booster fan of the present invention;

FIG. 4 illustrates interior support racks for polymeric membranes and semipermeable membrane devices of the present invention;

FIG. 5 illustrates representative clips for attaching polymeric membrane to internal support racks;

FIG. 6 illustrates an internal support rack with membrane clusters attached;

FIG. 7 illustrates an internal support rack with generator semipermeable membrane devices attached;

FIG. 8 illustrates an internal support rack with membrane clusters and generator semipermeable membrane devices attached;

FIG. 9 illustrates a representative sampling device exposure chamber of the present invention;

FIG. 10 illustrates a representative sampling device exposure chamber showing the attachment of semipermeable membrane devices; and, FIG. 11 illustrates an active air sampling tube.

DETAILED DESCRIPTION OF THE PREFERRED EMBODIMENT

The present invention provides for a constant concentration device, method and product, preferably with continuous flow, to overcome obstacles associated with exposure to and monitoring of complex mixtures of vapor phase chemicals in the environment. The present invention can be used to calibrate devices to monitor the vapor phase chemicals in the atmosphere and to supply constant concentration vapor phase mixtures of airborne chemicals for inhalation exposure studies, chemical photoactivation studies, synergistic/antagonistic toxicological studies of vapor phase chemical mixtures, exposure studies related to vapor phase chemical and biological agents, etc. Additionally, the present invention is useful in determining mechanisms/kinetics of vapor phase chemical reactions related to industrial processes and development of methods to control the release of vapor phase chemicals from industrial operations, power plants, petroleum production/refining operations, etc. Because the device functions to produce constant concentrations of mixtures of vapor phase chemicals, the present invention provides a means to directly assess organism exposure to complex mixtures of toxicological relevance, which is particularly useful in current techniques used in studies required by government environmental and health agencies.

As seen in the block diagram of FIG. 1, the present invention includes a device for delivering constant concentration 10 of a vaporized substance, as more detailed in FIGS. 2–11. One or more preferred embodiments of the present invention for generating mixtures of vapor phase chemicals are depicted in these FIGS. 2 through 11. Equivalent materials or components to those described herein may be used.

Referring to FIGS. 1 and 2, the present invention includes a core element or chamber 14 having a walled system or walls 40 defining an enclosed recyclable area 42. The walls 40 of the chamber 14 further define the enclosed recyclable area 42 as an integrated multi-component vapor tight system with the core element 14. Preferably the walls 40 include tubing configuration that is configured in a feed-back or doubling arrangement such as a rectangular arrangement, circular arrangement, square arrangement, triangular arrangement, etc., with a rounded rectangular or circular arrangement most preferred. Appropriate materials, such as numerous types of metal or less desirably polymeric pipe can be employed in the construction of the core element 14 ring used to house the materials employed in generating the mixture of vapor phase chemicals for ultimate delivery to the appropriate exposure system. The tubing configuration more preferably includes metal tubing, or less preferably includes polymeric or glass tubing, such as without limitation, metals of stainless steel, aluminum, copper, steel, nickel, galvanized steel, iron, etc, and combinations thereof, including combinations with non-metal components, and polymeric materials of polycarbonate, polyvinylchloride, high-density polyethylene, high-density polypropylene, co-polymers such as acrylonitrile/butadiene/styrene, and the like, and combinations thereof, including combinations with non-polymeric components. Any seams and/or joints occasioned by the construction of the chamber 14 are sealed in an air-tight manner, with appropriate sealing methods known by those skilled in the art for a particular structural composition.

The physical configuration of the device 10, particularly the enclosed recyclable area 42, of the present invention varies depending on the specific application and its scale. The circumference of the enclosed recyclable area 42 preferably ranges from about three (3) centimeter i.d. to about one (1) meter i.d., more preferably from about ten (10) centimeters i.d. to about one-half (2) meter i.d., and most preferably from about twenty (20) centimeters i.d. to about thirty (30) centimeters i.d. Although a circular or oval interior shape is preferred to decrease the likelihood of internal turbulence within the enclosed recyclable area 42, non-rounded shapes of the interior surface are permitted as this turbulence generally has minimal impact on the operation of the device 10.

The core element 14 of the present invention generates measurable vapor phase concentrations of test articles. As exemplified in FIG. 2, a core element 14 was constructed from eight-inch (20.32 cm) diameter aluminum heating ventilation and air conditioning (HVAC) duct pipe and four HVAC eight-inch (20.32 cm) aluminum 90<elbows forming a closed rectangular loop having outside dimensions of 44×58 inches (111.76×147.32 cm) and an internal volume calculated to be 155 liters. Other constructions of the core element 14 may be used as provided herein.

Figure 5:
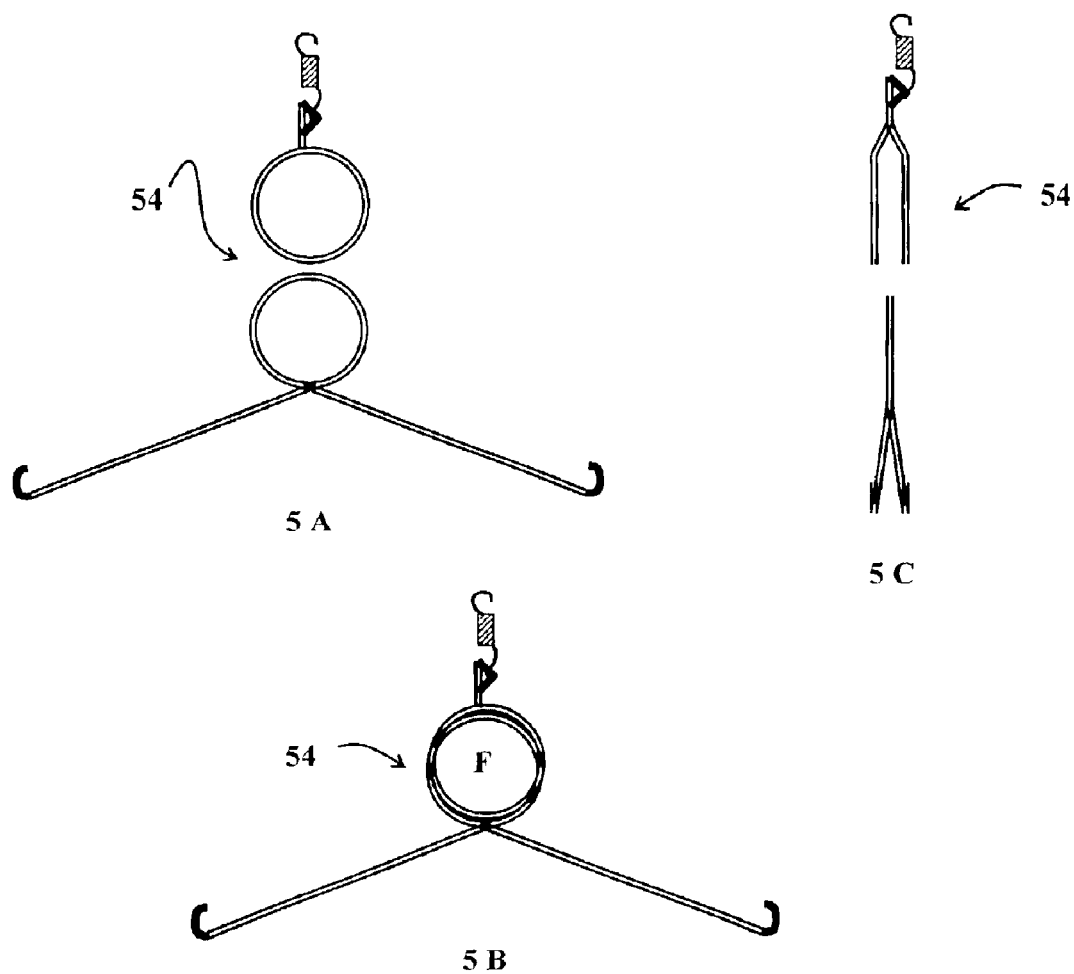
Figure 6:
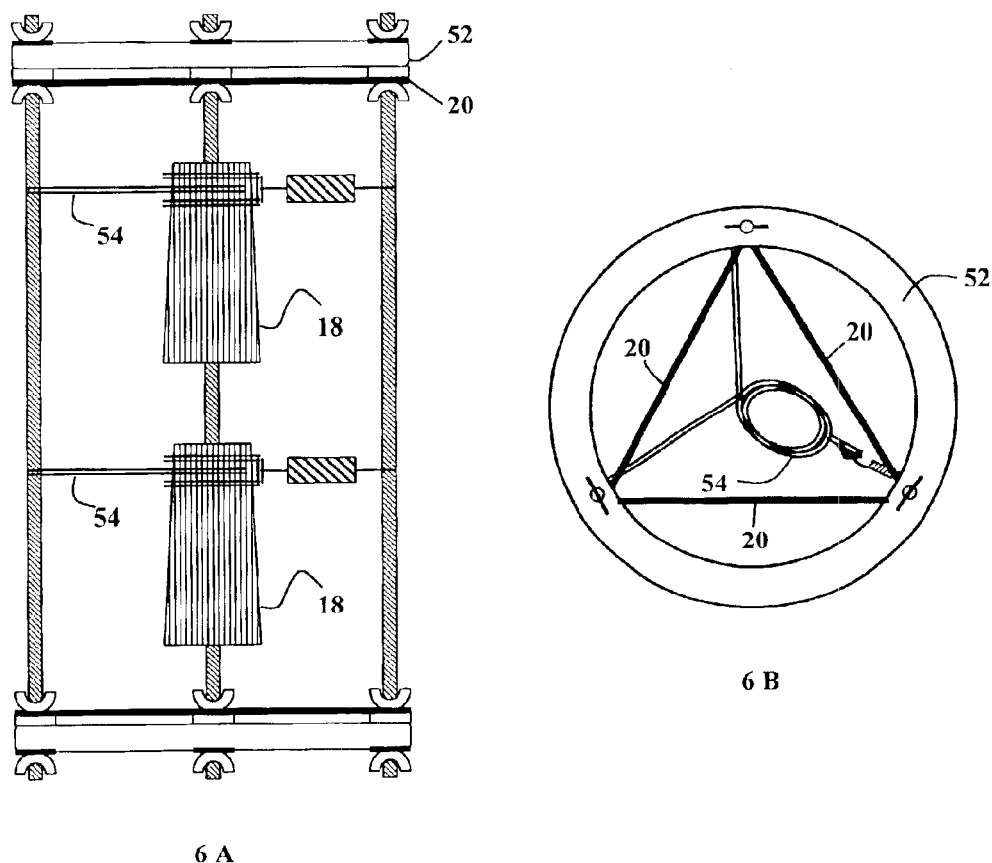
Figure 7:
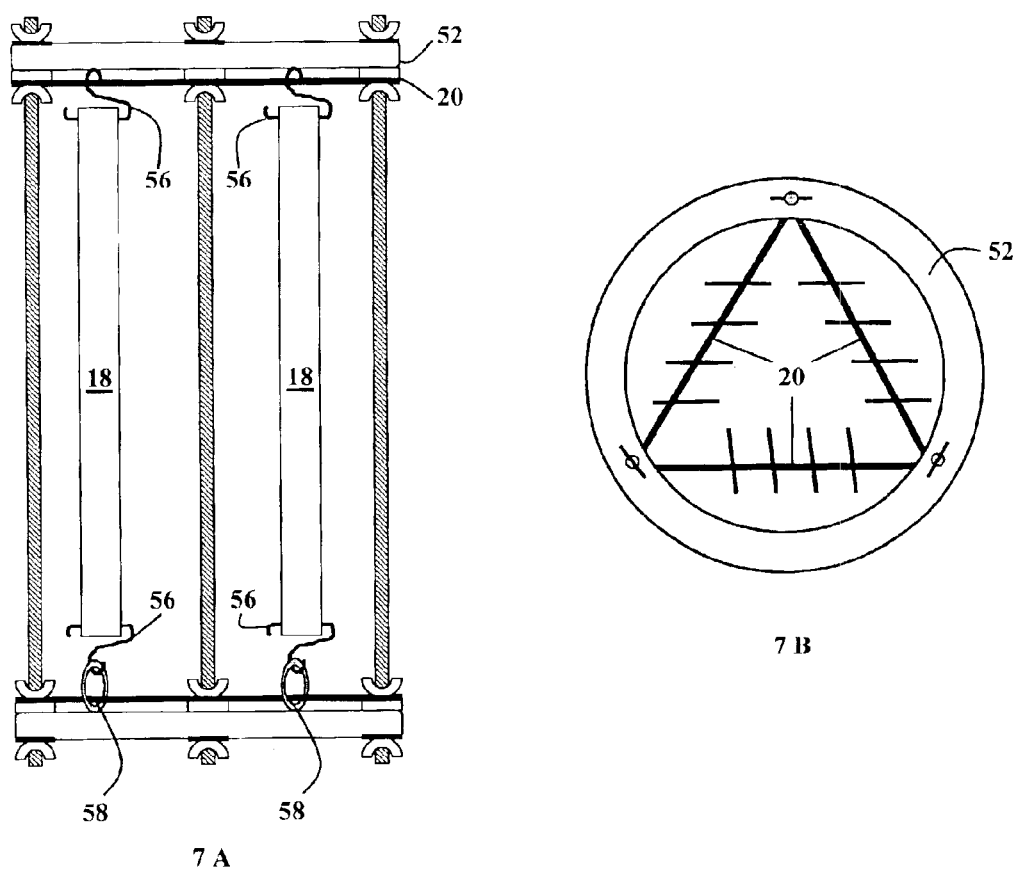
Figure 8:
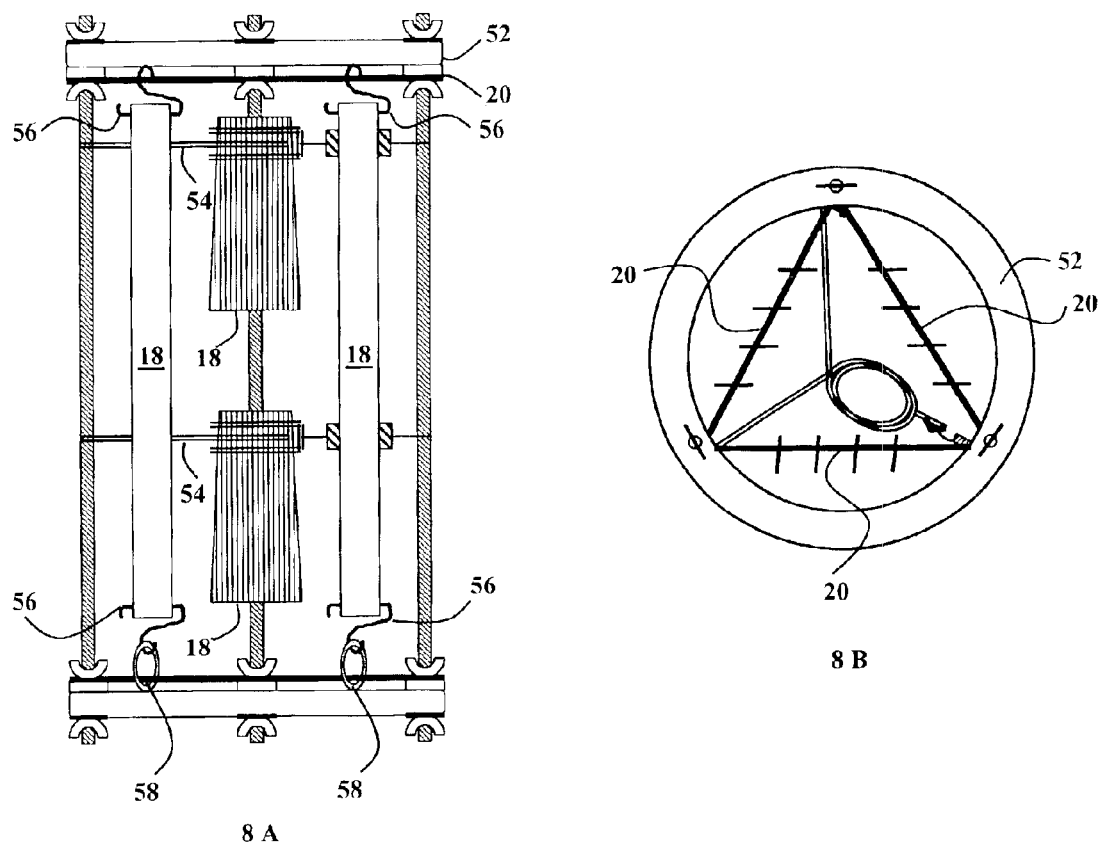
Figure 9:
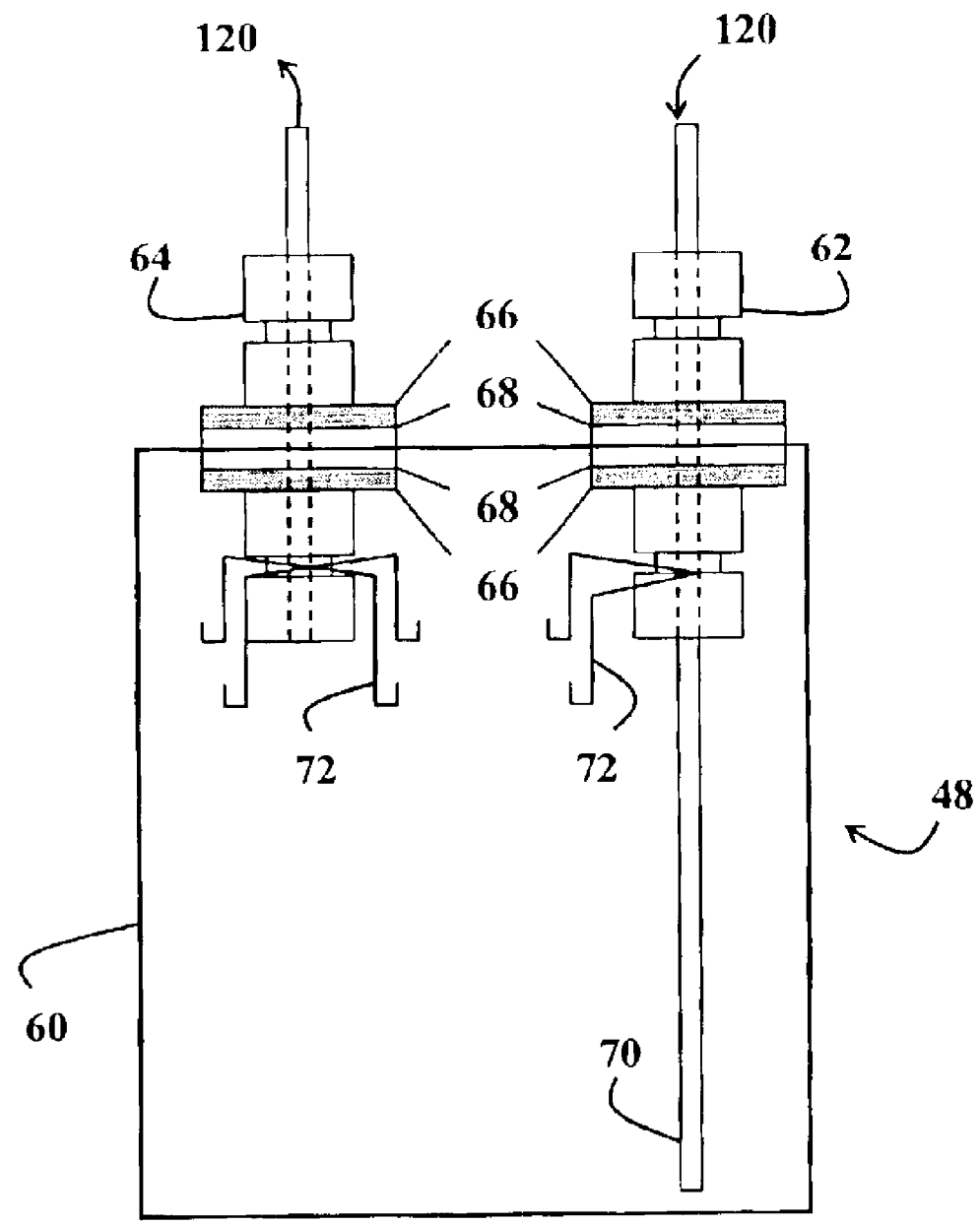
Figure 10:
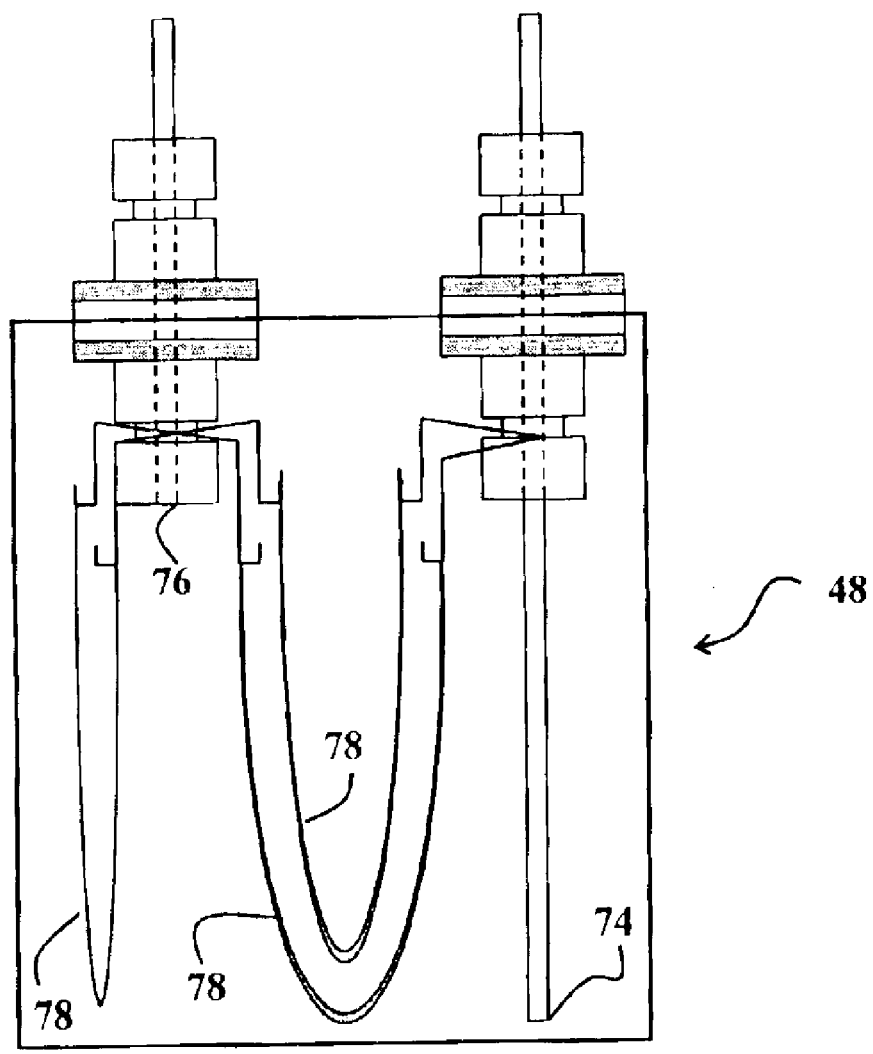

The device 10 includes a gaseous medium inlet 12 located through the walls 40 of the chamber 14. The gaseous medium inlet 12 is used to seal the interior of the enclosed recyclable area 42 of the chamber 14 from the exterior of the chamber in the absence of one or more gases 100 flowing into the chamber 14. The gas 100 includes any appropriate gas for combination with a given vaporized substance 110 for a given purpose, with the gas 100 preferably comprising atmospheric air that is more preferably filtered prior to entry into the chamber 14. Alternatively or in addition to environmental air, the gas 100 may include inert gases such as argon, nitrogen, helium, etc., reactive gases such as bromine, chlorine, etc., nutrient gases for increased biological survival times, or any other appropriate gas(es), and combinations thereof, for a given use. Preferably, the gaseous medium inlet 12 comprises a valve. The device 10 may further include a pumping device 46 for drawing gas through the gaseous medium inlet 12 from the exterior of the chamber 14 into the interior of the enclosed recyclable area 42. The pumping device 26 preferably includes an auxiliary pump and associated precision flow valves 32 used to provide (as required) un-dosed makeup air when multiple levels of vapor phase chemicals are desired in parallel exposure chambers.

Within the chamber 14, a circulating component 16 is used to circulate the gas 100 within the enclosed recyclable area 42. The circulating component 16 is communicatively aligned with the interior of the enclosed recyclable area 42 of the chamber 14, and is preferably located therein, and circulates and recycles the gas 100 within the recyclable area 42. Preferably, the circulating component 16 includes a fan, compressed gas, pressurized gas, pumps or other like circulating devices for movement of the gas 100. Most preferably the circulating component 16 comprises a fan to circulate the inputted gas 100 from the gaseous medium inlet 12 within the core element 14, and thereafter recycles the gas 100 within the enclosed recyclable area 42 forming a substance enhanced gas 120. Preferably, the circulating component 16 comprises a means to vary the displacement of the gas 100 (and/or substance enhanced gas 120) within the recyclable area 42. Optionally, auxiliary systems, such as an auxiliary ambient air inlet 28 connected to an auxiliary air pump 30, passing through an auxiliary manifold high precision flow valve(s) 34, into the substance reservoir 18 may be used to augment air flow and/or flush the chamber 14, as needed. Examples of the auxiliary air pump 30 include additional fan, pump, and the like, or other type of mechanisms that draw or push ambient air or specified gas 102 into the core element 14 and delivers, preferably through the auxiliary ambient air inlet 28, which more preferably includes one or more high precision flow valves 32, into the chamber 14. This provides at a controlled flow rate, constant concentrations of the mixtures of chemicals to a substance reservoir 18 (as more fully described below) either under inhalation exposure applications or for calibration of passive air samplers, etc. Flow rates within the core element 14 for the process of the present invention may be regulated as needed for a given use. Typically flow rates range from about 0.01 liters/minute to about 1000 liters/minute, with a more preferred range of from about 0.1 liters/minute to about 100 liters/minute, most preferably from about 1 liters/minute to about 10 liters/minute.

As exemplified in FIG. 3, the circulating component 16 is communicatively aligned with the interior of the enclosed recyclable area 42 of the chamber 14 for circulating the gas 100 within the recyclable area 42. An eight-inch (20.32 cm) duct booster fan 16, powered by a 110 volt shaded-pole induction motor and fitted with a five-bladed metal impeller, was inserted into and near the end of one of the core element 14 shortened lengths, shown in FIG. 2. The booster fan output 16 as shown in FIG. 3, rated at 420 $ft^3$ (12.6 $m^3$) per minute, was calculated to provide circulation of air 100 within the core element 14 at an un-impeded linear flow of 5.63 meters per second. Equivalent circulation components as that exemplified in FIG. 3 may be used as provided herein.

Again referring to FIGS. 1 and 2, also located within the chamber 14, the substance reservoir 18 is communicatively accessed to the recyclable area 42, also preferably therein, and is used for imparting the vaporized substance 110 (not shown in FIG. 1) into the gas 100 within the recyclable area 42 to create the substance enhanced gas 120 within the enclosed recyclable area 42. The substance reservoir 18 contains a vapor producing means to integrate a specified chemical or biological composition into the gas 100. As the circulating component 16 circulates, and re-circulates, the gas 100 passes through the enclosed recyclable area 42 (and through the area of the substance reservoir 18) and increasingly becomes saturated with the chemical or biological vaporized substance 110 until a steady state is achieved within the substance enhanced gas 120. In one preferred embodiment, the substance reservoir 18 comprises removable inserts.

Supports 20 for the substance reservoir 18 may include support racks 50, as exemplified in FIGS. 4A and 4B (side view and top view, repectively), collectively called FIG. 4, to support the substance reservoir 18. As seen in FIGS. 2 and 4, preferably the support racks are constructed to fit snugly inside each of the three of the four sections, or legs, of the core element 14. Rings 52, at the ends of each rack 50, are used to fix the substance reservoirs 18 in place. As shown in FIG. 4, for example, support racks 50 may be made from half inch aluminum tubing and connected with three equally spaced (equilateral triangle geometry) quarter inch 316 series stainless steel all-thread (quarter inch twenty thread) rods running axially to the leg of the core element 14. The support rack end rings 52, orientated perpendicularly to the particular leg of the core element 14, may be fastened to the all-thread rods using flat washers and wing nuts (all 316 series stainless steel). The rack supports 20 were constructed to serve as end supports for polymeric tubing containing lipid with a mixture of chemicals (herein after referred to as generator semipermeable membrane devices). Number 10 American Wire Gage (AWG) aluminum wire was formed into equilateral triangles at each end of the rack by wrapping the wire around the three axial all-thread rods between the end rings and interior wing nuts which hold the end rings to the rods. The generator semipermeable membrane devices (referred to herein as SPMD) were attached to these end wires using a stainless steel hanger 56 at one end and a stainless steel hanger and nylon wire-tic 58 at the other end. Bundles of polyethylene membrane (hereinafter referred to as membrane clusters) impregnated, via pervaporation, with chemicals were supported along the core element 14 centerline of the support racks 50 using clips 54, as shown in various configurations of FIGS. 5A, 5B and 5C, made from number 10 AWG aluminum wire and a stainless steel spring. Loading within the chamber 14 included generator semipermeable membrane devices and generator membrane clusters, with the support rack 50 loading shown in FIGS. 6A, 6B, 7A, 7B, 8A and 8B(side view and top view, respectively), collectively called FIG. 6, FIG. 7 and FIG. 8, respectively for like numbered subsets. The substance reservoir 18, with any accompanying components, may use alternative designs, methodologies and/or functions in addition to those exemplified in FIGS. 4–8, as provided herein.

The substance reservoir 18 includes any appropriate holding device or mechanism for dispersal of chemical and/or biological vapors within the chamber 14. Preferably, the substance reservoir 18 includes such compositions as nonporous synthetic polymeric films for the controlled generation of vapor phase chemicals and/or biologicals. Representative compositions include without limitation polyethylene, polypropylene, silicone and Silastic, polyvinylchloride, chlorinated polyethylene, chlorosulphonated polyethylenes, polyimides, polyethylene vinyl acetate copolymers, including laminates of microporous polymers with these nonporous polymers, etc. A preferred embodiment includes a tubular configuration, with the polymeric tubes having any appropriate reservoir capable of allowing one or more chemicals to effectively diffuse, including designs such as for example without limitation, layflat, semiturgid, turgid, etc., loaded with one or more chemicals and/or biologicals and mixtures of chemicals and/or biologicals (at times referred to solely as chemicals) directly through a pervaporation process. Alternatively, the polymeric tubes may contain media in which the mixtures of chemicals are dissolved to increase the mass of the chemicals available for release into the vapor state during the generation process. Such chemical retention media include, but are not limited to, lipids such as triolein, mixtures of triglycerides, silicone fluids, normal and reversed phase sorbents, high molecular weight organic liquids, inorganic liquids, etc. One preferred composition includes polyethylene, triolein, and calcined sodium sulfate. Thicknesses of the polymeric films may vary, as desired, with relatively thin polymeric films, such as ranging from about 0.0002 to about 0.0196 inches (5 to 500 $\mu$m) thickness being generally preferred for most applications because of the advantage of maximizing transport of the neutral organic chemical species through the membrane or from the retention medium through the membrane into the vapor state in a controlled manner for extended exposure periods. However, in the case of large-scale applications or for long exposure periods, such as for example, exceeding 120, 150 or 200 days and the like, the generator portion of the present invention is preferably constructed of thicker polymeric membranes to safely hold larger amounts of the sequestration medium (e.g., SPMD like configuration) and to increase the capacity of the polymer sheets to retain mixtures of chemicals introduced through the pervaporation process directly into the polymeric sheets. Large-scale applications include, for example, controlled environments within working spaces, care facilities, laboratories, etc., such as building, vehicles, hospitals, and the like, where the device 10 may constitute a component outside of or within the environmentally controlled area.

The surface area (of the polymeric film) to volume (of the enclosed media containing the mixture of chemicals) ratios used for the present invention can vary greatly depending on the nature of the particular application for the device 10, which may be determined by one skilled in the art in light of the disclosure herein. The larger surface area configurations permit greater total chemical flux into the enclosed vapor phase generation portion of the system per unit time, which increases the overall production of the vapor phase chemical or chemical mixtures. Such configurations can be employed in both air sampler calibration and exposure applications. For some large scale or extended exposure applications, adequate rates of production of vapor phase chemical or chemical mixtures may use large numbers or long lengths of tubing containing large amounts of the media containing the chemical or mixtures of chemicals, with the optimum dimensions, loading and configuration being determinable with ordinary experimentation. One example, without limitation, of a large scale configuration is as follows: approximately 2000 mL of liquid media (e.g., triolein) is placed in a three meter length of 15 centimeter wide layflat, low density polyethylene tubing having a wall thickness of 0.01 to 0.03 centimeters. The ends of the layflat tubing are heat sealed, secured with large clamps, etc., and placed in the enclosure of the core element ring portion of the system. The device so configured can be deployed in multiple single large-scale configuration arrays or in cluster arrays. By employing many of these large-scale configurations in the vapor phase containing systems, constant concentrations of vapor phase mixtures of chemicals can be readily produced for use in extended exposure applications. In addition to the SPMD like configurations described above, it can be readily seen that large polymeric sheets, multiple layers of polymeric sheets, or sheets of greater thickness, all designed to increase the effective surface area and/or mass of chemical present of the configuration can be used to provide for the generation of chemical vapors for extended time periods, such as for example without limitation, partly sealed polymeric film sheets which provide a very large surface area, can be arranged in bundles or arrays, etc., secured by means of a frame or other deployment arrangement, filled with the appropriate retention media, and subsequently sealed. Preferably a combination of various chemical vapor generation techniques may be used to facilitate the design and implementation of extended exposures, e.g., using any of the configurations individually or in combination provides a wide variety of alternate embodiments.

Molecular size and polarity are physicochemical-related factors that limit the transport of organic chemicals through nonporous polymers. For example, the permeability of small molecular weight organic molecules through polyethylene (at constant temperature and pressure) decreases according to increasing polarity (i.e., approach to ionic state) of functional groups generally as follows: halogenated hydrocarbons, hydrocarbons, ethers, esters, ketones, aldehydes, nitro-derivatives, alcohol and acids. Consequently, this type of resistance to mass transfer or diffusion reduces the effectiveness of very nonpolar polymers such as polyethylene, polypropylene, etc., for applications dealing with polar chemicals such as phenols, alcohols and organic acids. As the chemical moiety increasingly becomes polar enough to be ionic (e.g., $Hg^{+2}$) it decreases in its ability to diffuse through the nonporous hydrophobic polymer, which limits transport of such ionic chemicals. Accordingly, individual chemicals diffuse from the membrane to the exterior surface and evaporate as chemical vapors into the atmosphere within the system. This process is controlled by the individual chemical species=$K_{polymer/air}$ partition coefficient and the thickness of the Nerst air-boundary layer. This process ensures that all chemicals within mixtures behave independently of other chemicals within the mixture, with the process operative in all ambient atmospheres.

With the chamber 14 enclosing the substance reservoir 18 communicatively accessed to the interior of the enclosed recyclable area 42, this permits a functioning device 10 for imparting the vaporized substance 110 into the gas 100 within the enclosed recyclable area 42. The substance reservoir 18 preferably includes a series of nonporous polymeric tubes containing a liquid retention medium with a singular chemical or mixtures of various masses of chemicals, polymeric membranes of various thickness containing, through a pervaporation processes, mixtures of various masses of chemicals, other media, e.g., normal and reversed phase chromatographic materials, glass beads, ionic exchange resins, polymeric fibers, etc., coated with mixtures of chemicals. With placement of chemicals in the substance reservoir 18 in the configurations, as described herein, in the sealed core element 14 portion of the device 10, air may move, or be forced, such as at constant flow, through the device 10, making intimate contact with the substance reservoir 18 of the device 10 which provides an active regimen for producing constant concentrations of vapor phase chemical mixtures.

The polymeric tube employed as part of the substance reservoir 18 of the present invention preferably includes a thin-walled nonporous polyethylene, polypropylene, polyvinyl chloride, silicone, etc. Additionally, a thin layer of a nonporous polymer can be grafted or laminated to a thicker microporous polymer such as microporous polypropylene to increase strength. Nonporous membranes used in the present invention may be characterized by liquid-like and solid regions of the polymer, and in place of air filled fixed pores, transient cavities in the liquid-like regions. The size of these transient cavities in nonporous polymers is preferably small (such as for example, about # 10Δ in cross sectional diameter) which may limit the rate of chemical release from the membrane. Because the uptake rate and the dissipation rate of chemicals in these components are integral parts of an isotropic process, the polymeric tubing, containing a retention medium or polymer sheets of predetermined thickness in concert with the Nerst air-boundary layer, function to provide a controlled release of the mixtures of chemicals. In addition, the polymer tubes may be configured to contain solid materials containing mixtures of sorbed chemicals, with such configuration determinable by one skilled in the art in light of the disclosure herein. These nonporous polymer tubes or sheets preferably are hydrophobic in nature and virtually non-permeable to charged or polar species. As such, the present invention provides a means of producing bioconcentratable organic chemicals as vapor phase molecules without use of solvents, aerosols or particulate matter. Water as either vapor or liquid resists passage through the transient cavities which effectively eliminates the requirement for humidity control in the vapor phase production system.

In addition to numerous nonporous polymeric materials suitable for use as tubing or sheets, the retention medium employed in the tubing can be tailored to accommodate a broad array of chemicals. Examples include, but are not limited to, neutral lipids such as triolein, other triglycerides, silicone fluids, ionic liquids, chromatographic materials, polymeric fibers, glass beads, metal beads, glass wool, etc. The nonporous polymeric material functions to control the release of the vapor phase molecules, as distinct molecules and not aerosols, through controlled diffusion of individual chemicals (based on the physicochemical characteristics of the individual chemicals) in the mixture into the gaseous phase. Subsequent to production of true vapor phase chemical mixtures, the system functions to deliver the mixture of chemicals at constant concentrations and constant flow rates to the exposure chamber(s), which include, for example without limitation, either an inhalation exposure configuration or an enclosed calibration configuration. The present invention can accommodate different temperatures, flow rates, and vapor phase concentrations of the mixtures of chemicals. In addition to these advantages, the present invention provides an easily decontaminated, reusable system suitable for complex mixtures of chemicals.

The major controlling factors for the production of vapor phase molecules includes the selective diffusion of neutral chemical species through the nonporous polymer, volatilization, and the subsequent forced air transport of the individual molecules of each chemical in the mixture through the production portion of the system into the exposure chambers. This process enables the controlled delivery of constant concentrations of vapor phase chemicals from one medium (the polymeric sheets, tubes, etc.) into the gas phase test chamber within the exposure system. This system is capable of generating the aforementioned mixture of chemical vapors in a controlled and reproducible manner during extended exposure periods (e.g., greater than 30, 45, 60, 90, etc. days).

For analytical measurements of vapor phase chemicals, residues are readily trapped for example by employing a train of polyurethane foam plugs and carbon impregnated polyurethane foam plugs, or by using other readily available chemical trapping techniques. Sequestered residues are easily recovered and analyzed using organic solvent elution of the plugs and standard analytical approaches, eg., gas chromatography with a variety of detectors or other instrumental techniques as appropriate. Such concentration determinations are readily accomplished by using a separate, but equal, gaseous medium flow through the system. Thus, the system provides a means of providing exposures to complex mixtures of vapor phase chemicals and a means of independently (i.e., direct measurement of vapor phase concentrations) verifying the vapor phase chemical concentrations during the exposure.

As described previously, the cavities (transient openings resulting from the thermally mediated motions of the polymer chains) in nonporous membranes may be about 10Δ in cross sectional diameter. Consequently, the larger the chemical, the more restrictive becomes the permeation path through the polymer film. In the case of mixtures of chemicals, the physicochemical characteristics of each individual chemical control its transport through the membrane. Therefore, unless reactions between chemicals occur, little impedance to the diffusion of mixtures of chemicals through the polymer is probable due to interactions between chemicals in the mixture. The diffusion process through the nonporous polymer is typically limited to a molecule by molecule process. Constant diffusion from the retention medium and constant volatilization into the vapor phase results in a constant concentration of the vapor phase chemicals through time. Demonstration of this theory is provided by the data presented in Table 1, listed below. Table 1 shows results of vapor phase concentrations using Chlorpyrifos, trans-Chlordane, p,p=–DDT, Phenanthrene, Pyrene and Chrysene, examples of widely occurring airborne contaminants. From the data in Table 1, it is seen that for chemicals having a very wide range of physicochemical characteristics, the variation in the vapor phase concentration of each individual chemical in the mixture ranges from about 7% to about 22% with all but one test chemical exhibiting concentrations that varied by about 15% during 60 days of constant operation. It is readily recognized from these results that each vapor phase chemical behaved independently and resulted in the production of very reproducible, constant airborne concentrations. Consequently, the present invention provides a means of producing a broad spectrum of vapor phase chemicals for a wide variety of applications, independent of mechanical, thermal, aerosol generation, etc., processes.

the size and diameter of the chamber being determinable by one skilled in the art for such use.

Figure 2:
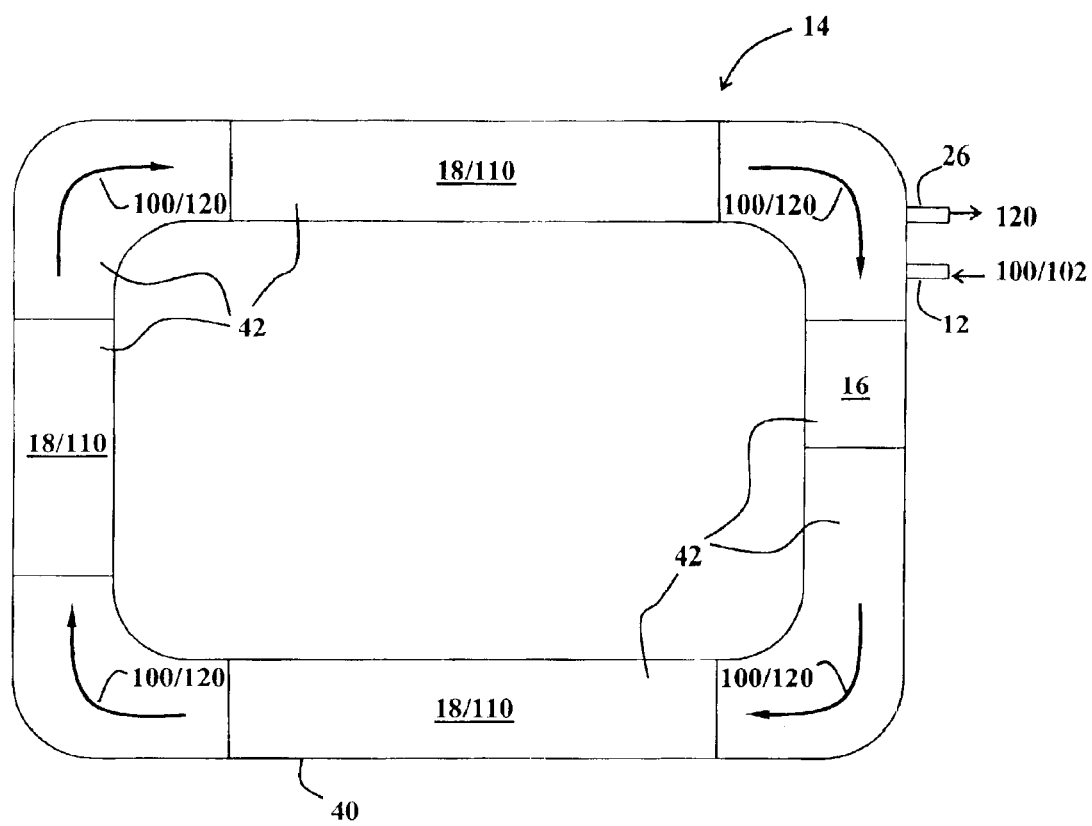
Figure 3:
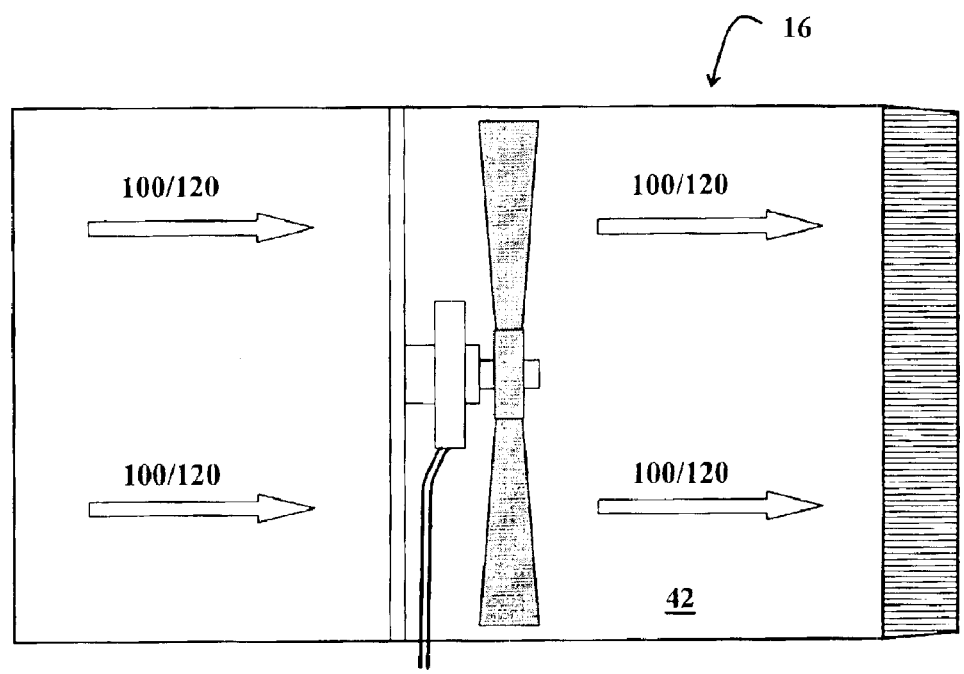
Figure 3:
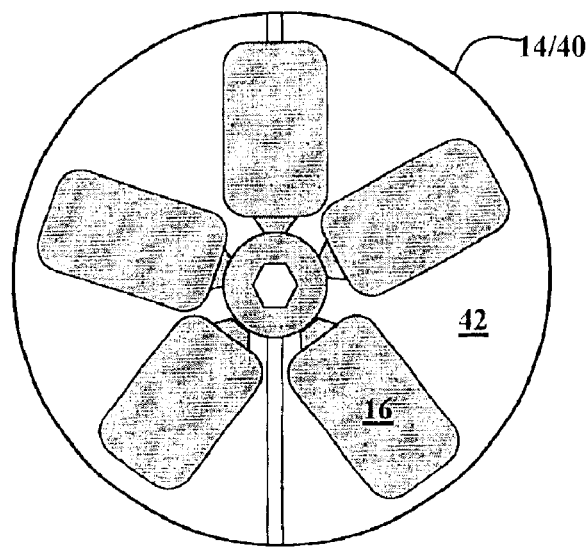
Figure 4:
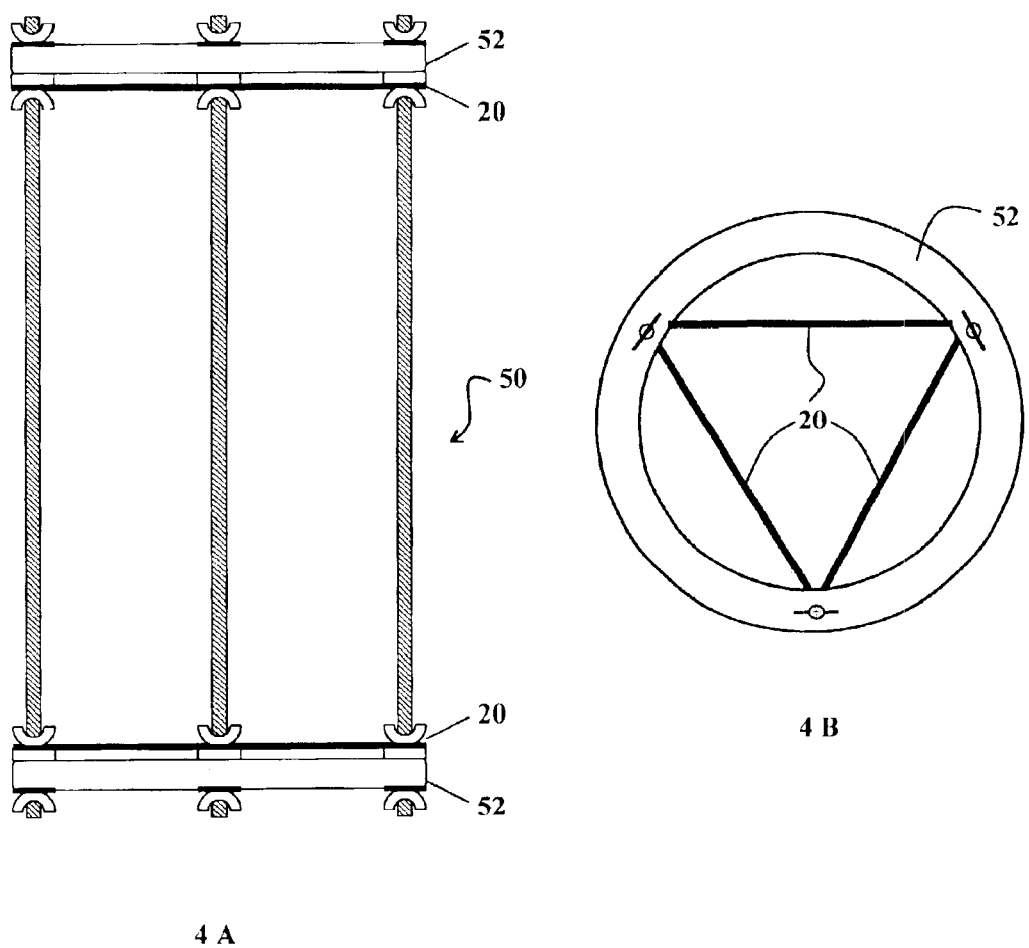
Figure 11:
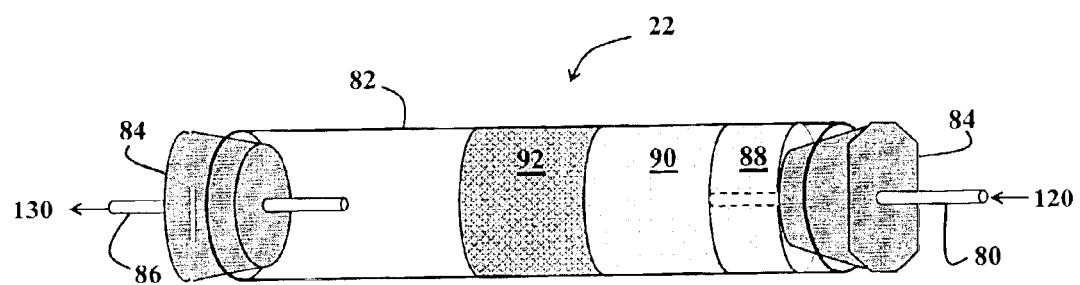

As further seen in FIGS. 1 and 2, the device 10 of the present invention further includes a substance enhanced gaseous medium outlet 26 from the enclosed recyclable area 42 that seals the interior of the recyclable area 42 of the chamber 14 from the exterior of the chamber 14 when the substance enhanced gas 120 (not shown in FIG. 1) is not flowing out of the chamber 14. Additional components may include active air sampling tubes 22 (shown in FIG. 11) and/or one or more flow meters 24 positioned within the chamber 14 prior to the substance enhanced gas 120 exiting the chamber 14. Preferably the substance enhanced gaseous medium outlet 26 comprises a flow controlled device or manifold.

In a preferred embodiment, the device 10 of the present invention may be used to calibrate the air sampler, described in U.S. Pat. No. 5,395,426 to Huckins et al., to produce and deliver a constant concentration of complex mixtures of vapor phase chemicals, while eliminating any emissions of the test chemicals. The integrative sampler described in Huckins et al. provides a sampling device for a wide variety of vapor phase organic chemicals from the atmosphere. Used in conjunction with the Huckins et al. sampler, the present invention provides an easily decontaminated, reusable system allowing the production and delivery of complex mixtures of vapor phase chemicals in a safe, cost effective, and reproducible manner from the device 10 which provides an efficient and reusable system to produce and

TABLE 1

Vapor Phase Concentrations of Select Chemicals Over Time (ng per cubic meter)

| Study Day | Chlorpyrifos | trans-Chlordane | p,p = -DDT | Phenanthrene | Pyrene | Chrysene |
|---|---|---|---|---|---|---|
| 0 to 3 | 3630 | 252 | 150 | 12800 | 772 | 24.7 |
| 3 to 6 | 3110 | 224 | 123 | 11600 | 772 | 23.5 |
| 6 to 9 | 3410 | 250 | 149 | 12200 | 882 | 28.9 |
| 9 to 12 | 3680 | 234 | 125 | 12700 | 882 | 33.1 |
| 12 to 15 | 3210 | 241 | 146 | 12200 | 937 | 33.9 |
| 15 to 18 | 3240 | 231 | 131 | 12200 | 882 | 31.7 |
| 18 to 21 | 2760 | 259 | 158 | 13400 | 970 | 24.1 |
| 21 to 24 | 2670 | 261 | 167 | 13300 | 1000 | 23.1 |
| 24 to 27 | 2640 | 252 | 148 | 12400 | 976 | 23.7 |
| 27 to 30 | 2900 | 250 | 154 | 12500 | 981 | 34.3 |
| 30 to 33 | 2490 | 225 | 146 | 11000 | 816 | 20.4 |
| 33 to 36 | 2990 | 222 | 181 | 13700 | 1080 | 33.2 |
| 36 to 39 | 3110 | 212 | 167 | 12800 | 932 | 36.1 |
| 39 to 42 | 2810 | 191 | 171 | 11700 | 893 | 34.0 |
| 42 to 45 | 2620 | 194 | 152 | 12800 | 838 | 24.5 |
| 45 to 48 | 2790 | 219 | 148 | 13300 | 921 | 24.6 |
| 48 to 51 | 2760 | 216 | 153 | 14300 | 888 | 26.6 |
| 51 to 54 | 2260 | 168 | 151 | 10700 | 711 | 20.2 |
| 54 to 57 | 2400 | 187 | 142 | 11400 | 810 | 17.8 |
| 57 to 60 | 2130 | 182 | 141 | 12100 | 799 | 16.5 |
| Mean = | 2880 | 224 | 150 | 12400 | 887 | 26.7 |
| STDEV = | 420 | 28 | 14 | 910 | 91 | 6.0 |
| RSD (%) = | 15 | 12 | 10 | 7.3 | 10 | 22 |

The vaporized substance 110 comprises a chemical or biological substance that preferably includes such substances as a volatile organic, semi-volatile organic or other chemical substances having from about a log $K_{oa}$# 13 (octanol/air partition coefficient). Preferably the vaporized substance 110 comprises a chemical substance for calibration purposes, or a biological substance for therapeutic purposes, which may encompass large-scale uses, such as complete buildings, or small-scale uses such as cages, with deliver in a controlled manner, constant concentrations of vapor phase chemicals, with additional advantages of limited mechanical and power requirements, and use in an integrative manner for extended periods of time, such as weeks, months, etc.

In one alternative embodiment, the device 10 can be operated in essentially a reverse sequence, i.e., air at a constant flow can be passed (either filtered or unfiltered) through the enclosed core element ring 14 containing semipermeable membrane devices (SPMDs) employed as integrative air samplers (see e.g., U.S. Pat. No. 5,395,426, Huckins, et al. 1995). Following exposure of the SPMD air samplers (other integrative air sampler may also be used), the air samplers are processed, the extract subjected to any of a variety of residue enrichment and fractionation techniques, and the extracts analyzed for airborne organic chemicals. By employing the present invention as a means of exposing an integrative sampler to a known volume of air at a constant flow for extended periods, it is possible to obtain time-weighted average (TWA) concentrations of vapor phase airborne mixtures of chemicals. Such an arrangement can be employed for analytical applications, reducing industrial exposures, remediation efforts and the like.

The device 10 prepares and delivers constant concentrations of mixtures of vapor phase chemicals to a specified point, such as to assess the average exposure of humans and other living things to chemicals via respiration, to calibrate monitoring approaches critical for defining the presence of atmospheric organic chemical contaminants, to define the optimum control methods for minimizing vapor phase emissions and to determine the potential synergism and/or antagonism of toxic effects resulting from respiratory exposure to mixtures of vapor phase chemicals. Because of the minimal use of mechanical systems and the incorporation of inert materials within the device 10, the device 10 is relative inexpensive to assemble, readily decontaminated and reusable. The device 10 incorporates a preferred zero emission design, effectively eliminating potential exposure of researchers and other workers employing the system. The device 10 provides a means of calibrating air samplers, conducting inhalation exposure studies incorporating individual vapor phase compounds to complex mixtures of vapor phase chemicals, determining potential synergistic or antagonistic toxic effects of mixtures of chemicals during exposure of organisms, optimizing conditions for reaction of vapor phase chemicals, designing approaches to control and eliminate emissions of vapor phase chemicals to the atmosphere, assessing the effectiveness of technology for protecting against chemical warfare agents and other such uses related to monitoring and/or regulating vapor phase chemicals, particularly for toxic organic species.

While producing and delivering constant concentrations of vapor phase mixtures of chemicals, the device 10 remains isolated from environmental influences and produces true vapor phase chemicals based on the inherent physicochemical characteristics of the chemical(s) of interest. The device 10 further provides enhanced precision for generation and delivery of vapor phase chemical mixtures for a wide variety of applications. In addition, the present invention is capable of utilizing highly biologically available airborne chemical species, i.e., readily respirable vapor phase, thus providing a mechanism for calibrating integrative air samplers for the most biologically relevant assessment of organism exposure, and for organism exposure to complex mixtures of biologically available vapor phase chemical mixtures. Also, the design of the present invention prevents elevated back pressure and facilitates generation and delivery of vapor phase chemical mixtures at a wide variety of flow regimens.

As vapor phase chemicals are produced based on the physicochemical characteristics of each individual chemical in the mixture relative to the pervaporation process, this replicates atmospheric exposures which results in improved precision of either air sampler calibration or the environmental relevance of organism exposure, particularly for laboratories that do not routinely conduct such research.

A constant concentration of a vaporized substance is delivered using the device 10 by moving gas 100 through the gaseous medium inlet 12 into the interior of the enclosed recyclable area 42, which is then circulated through the enclosed recyclable area 42 in a recycled manner. As the gas 100 is recycled, vaporized substance(s) 110 are continuously imparted therein to a steady state. This created substance enhanced gas 120 is delivered through the substance enhanced gaseous medium outlet 26, preferably at a continuous flow, for use. The delivered constant concentration vaporized substance product produced by the above-detailed process preferably includes either a calibrating, exposure or therapeutic substance. Under conditions where the physiological responses to vapor phase mixtures of specific chemicals are known, the present invention is particularly applicable for therapeutic applications.

As such the present invention provides an air stream that contains measurable levels of vapor phase chemical (or biological) mixtures maintained at constant concentrations, such as air stream maintained under conditions of constant flow, which providing a highly reproducible exposure condition per sampling device, i.e., per semipermeable membrane device (SPMD) contained within the exposure chamber. The product, resulting from a preferably self-contained, closed system (and non-permeable with respect to vapor phase chemicals), remains essentially free from any inadvertent introduction of targeted test chemicals (i.e., the mixture of vapor phase chemicals) into the ambient environment.

As increased temperatures are generally believed to result in increased diffusion rates of small neutral organic molecules through a particular polymeric film (see e.g., Sololev, I. et al., Ind. Chem. 1957,49,441; addressing the effect of both temperature and pressure on the permeability of methyl bromide in polyethylene), an increase in temperature within the present invention is expected to result in an increase in the amount of vapor phase chemicals through both an increase in the volatility of the chemical with increasing temperature and by an increase in the rate of diffusion of chemicals to the exterior surface of the polymer tube or sheet with increasing temperature. Additionally, although exceptions have been observed with organic molecules, increased atmospheric pressure can be expected to result in some increase in the permeability of the neutral organic chemical species through nonporous polymers. However, the overall effects of atmospheric pressure under ambient conditions generally are expected to be minimal.

The present invention is particularly useful by governmental agencies, such as United States Governmental agencies including but not limited to the Environmental Protection Agency (EPA), National Institute of Health (NIH), National Cancer Institute (NCI), Department of Energy (DOE), Department of Defense (DOD), National Institute of Occupational Safety and Health, (NIOSH), Occupational Safety and Health Administration (OSHA), National Institutes of Environmental Health Sciences (NIEHS), etc., and state health agencies, public utilities, and the like, to investigate and solve problems associated with exposure to complex mixtures of respirable vapor phase chemicals.

EXAMPLE 1

A device having a core element of the present invention and used to generate measurable vapor phase concentrations of test articles was constructed from eight-inch (20.32 cm) diameter aluminum heating ventilation and air conditioning (HVAC) duct pipe and four HVAC eight-inch (20.32 cm)

aluminum 90< elbows forming a closed rectangular loop having outside dimensions of 44×58 inches (111.76×147.32 cm) and an internal volume calculated to be 155 liters. An eight-inch (20.32 cm) duct booster fan, powered by a 110 volt shaded-pole induction motor and fitted with a five-bladed metal impeller, was inserted into and near the end of one of the core element short legs. This booster fan was rated at 420 ft$^3$ (12.6 m$^3$) per minute, and was calculated to provide circulation of gas within the core element at an un-impeded linear flow of 5.63 meters per second. Two holes were cut into the elbow on the low-pressure side of the booster fan, i.e., on the up-stream side of the fan, for ambient air inlet and test air outlet. The outlet port was positioned near the outer edge of the core element and further up-stream than the inlet port, positioned near the inner edge of the core element. These ports were fitted with quarter inch brass Swagelok bulkhead connectors, which were sealed to the walls of the core element using flat washers made from Teflon and 316 series stainless steel. Support racks were constructed to fit snugly inside each of the remaining three legs of the core element. Rings, at the ends of each rack, were made from half inch aluminum tubing and were connected with three equally spaced (equilateral triangle geometry) quarter inch 316 series stainless steel all-thread (quarter inch twenty thread) rods running axially to the leg of the core element. These support rack end rings, orientated perpendicularly to the leg of the core element, were fastened to the all-thread rods using flat washers and wing nuts (all 316 series stainless steel). To serve as end supports for layflat polymeric tubing containing lipid with a mixture of study test chemicals, (herein after referred to as generator semipermeable membrane devices), number 10 American Wire Gage (AWG) aluminum wire was formed into equilateral triangles at each end of the rack by wrapping the wire around the three axial all-thread rods between the end rings and interior wing nuts which hold the end rings to the rods. The generator semipermeable membrane devices were attached to these end wires using a stainless steel hanger at one end and a stainless steel hanger and nylon wire-tie at the other end. Bundles of polyethylene membrane (herein after referred to as membrane clusters) impregnated, through pervaporation, with study test chemicals were supported along the centerline of the support racks using clips made from number 10 AWG aluminum wire and a stainless steel spring. The core element (including interior support racks and booster fan) was cleaned by solvent rinsing prior to loading with generator semipermeable membrane devices and generator membrane clusters. All seams and joints in the HVAC aluminum duct pipe and elbows were sealed using aluminum duct tape on the exterior of the core element. A Cole-Parmer diaphram vacuum/pressure pump, model number U79200-30, with all wetted parts Teflon coated, was used to provide the air stream for the test system (Cole-Parmer Instrument Company, Vernon Hills, Ill.). The inlet port of the vacuum/pressure pump (i.e., the vacuum side of the pump head) was connected to the outlet port of the core element. This connection, and all other connections not otherwise specified, was made with a minimum length of quarter inch Teflon tubing fitted with quarter inch brass Swagelok compression fittings. Two Swagelok union cross connectors were coupled to form a six branch manifold. One branch served as the manifold inlet, which was connected to the outlet port of the vacuum/pressure pump (i.e., the pressure side of the pump head). A quarter inch Swagelok M Series stainless steel metering valve (St. Louis Fluid System Technologies, Fenton, Mo.) was connected to each of the remaining five manifold branches. Each valve, because of their common input, provided air streams of identical composition. Precise flow control of the individual air streams, from the core element to the individual exposure chamber, maintained the air stream under constant flow conditions.

Exposure chambers 48 were designed as air sampling device calibration units and were constructed from vapor tight quart paint cans 60 (Freund Container, Inc., Chicago, Ill.), shown in FIG. 9 (not to scale). Two holes were cut into the lid of each paint can for air stream inlet and outlet. These ports were fitted with quarter inch brass Swagelok bulkhead connectors, for inlet 62 and outlet 64, sealed to the lid using flat washers made from Teflon 68 and 316 series stainless steel 66. To insure the highest degree of turbulence possible within the exposure chamber, a length of Teflon tubing 70 was fitted into the exposure side, i.e., the inside of the can, of the inlet port bulkhead connector 62, to extend to within two mm of the bottom of the chamber. This geometry directed the air stream flow against the flat bottom of the chamber producing turbulence. A series of three yokes 72 were formed using number 18 AWG stainless steel wire to support the air sampling devices, specifically semipermeable membrane devices. One yoke was attached to the semipermeable membrane device exposure chamber inlet port bulkhead connector 62 (i.e., inside the can), and the other two were attached to the outlet port bulkhead connector 64, shown in FIG. 10 (not to scale). Referring to FIG. 10, an airstream inlet 74, airstream outlet 76 and SPMDs 78 looped between end of the yokes 72 are shown. The inlet port of each semipermeable membrane device exposure chamber was attached to the respective outlet end of the appropriate metering valve. A 24 mm i.d. by 184 mm borosilicate glass tube 82 having a wall thickness of 2 mm was used to hold the polyurethane foam (PUF) 90 and carbon impregnated PUF (PUF-C) 92 active air sampling tubes 22 (in order of air-stream flow), as shown in FIG. 11. A quarter inch Teflon tube 80 extending one half inch (1.27 cm) through a silicon-rubber laboratory stopper (no. 4) was used to connect the air sampling tube to the output port of the exposure chamber (specifically, in this embodiment, the semipermeable membrane device exposure chamber). A half-length PUF plug 88 with a quarter inch axial (i.e., down the middle of the plug) hole was fitted over the outlet end 86 of the Teflon tube from the semipermeable membrane device exposure chamber to prevent the un-scrubbed air stream from making contact with the silicon rubber stopper 84. This half-length PUF plug 90 was treated as part of the PUF active air sampling tube. A Cole-Parmer 100 mm direct read acrylic flow meter, model number U-32458-52, was used to monitor the air stream flow rates for each semipermeable membrane device exposure chamber in the test system (Cole-Parmer Instrument Company, Vernon Hills, Ill.).

The air stream exhaust 130, at this point, has been scrubbed by the active air sample traps and is free of both test chemicals and any volatile organic contaminants present in the ambient laboratory air, which was drawn into the core element by the vacuum/pressure pump.

This fills the design objective of being non-polluting or more to the point, a closed, self-contained system. A short length of quarter inch Teflon tube extending one half inch through a silicon rubber laboratory stopper was used to connect the air sampler tube to the bottom of the flow meter using quarter inch (0.635 cm) laboratory grade latex tubing. The scrubbed air stream exits the test system at the top of the flow meter and is vented into a laboratory fume hood.

The foregoing summary, description, and examples of the present invention are not intended to be limiting, but are only exemplary of the inventive features which are defined in the claims.

What is claimed is:

1. A device for delivering constant concentration of a vapor phase chemical, comprising:
   a chamber having walls defining an enclosed recyclable area;
   a gaseous medium inlet located through the walls of the chamber capable of sealing the inner of the chamber from the exterior of the chamber in the absence of allowing gas to flow into the chamber;
   a circulating component communicatively aligned with the interior of the chamber capable of circulating the gas within the recyclable area;
   a vapor phase chemical generator, comprising at least one removable insert, communicatively accessed to the interior of the recyclable area for imparting a vapor phase chemical substance into the gas within the recyclable area; and,
   a substance enhanced gaseous medium outlet from the recyclable area capable of sealing the inner of the chamber from the exterior of the chamber in the absence of allowing the substance enhanced gas to flow out of the chamber.

2. The device of claim 1, wherein the at least one removable insert comprises a polymeric membrane containing a chemical substance.

3. The device of claim 1, wherein the vapor phase chemical substance comprises a chemical or biological substance.

4. The device of claim 3, wherein the vapor phase chemical substance is a chemical substance selected from the group consisting of volatile organic, semi-volatile organic and chemical substances having a log $K_{oa}$ # 13.

5. The device of claim 1, wherein the vapor phase chemical substance comprises a biological substance.

6. The device of claim 1, wherein the chamber comprises an impermeable composition selected from the group consisting of steel, glass and polymeric composites.

7. The device of claim 1, wherein the gaseous medium inlet comprises a valve.

8. The device of claim 1, wherein the substance enhanced gaseous medium outlet comprises a flow controlled device or manifold.

9. The device of claim 1, wherein the circulating component is selected from the group consisting of fan, compressed gas, pressurized gas and pumps.

10. The device of claim 9, wherein the circulating component comprises a fan.

11. The device of claim 1, wherein the circulating component is located internally within the enclosed area of the recyclable area.

12. The device of claim 2, comprising a plurality of removable inserts.

13. The device of claim 1, wherein the recyclable area comprises a tubular configuration.

14. A controlled environment comprising the device of claim 1.

15. A process for delivering a constant concentration of a vapor phase chemical substance, comprising the steps of:
   providing a device for delivering constant concentration of a vapor phase chemical substance comprising a chamber having walls defining an enclosed recyclable area, a gaseous medium inlet located through the walls of the chamber capable of sealing the inner of the chamber from the exterior of the chamber in the absence of allowing gas to flow into the chamber, a circulating component communicatively aligned with the interior of the chamber capable of circulating the gas within the recyclable area, a vapor phase chemical generator communicatively accessed to the interior of the recyclable area for imparting a vapor phase chemical substance into the gas within the recyclable area and a substance enhanced gaseous medium outlet from the recyclable area capable of sealing the inner of the chamber from the exterior of the chamber in the absence of allowing the substance enhanced gas to flow out of the chamber;
   moving gas through the gaseous medium inlet into the interior of the recyclable area;
   circulating the moved gas within the recyclable area sufficient to recycle the gas within the recyclable area;
   continuously imparting vaporized substance into the circulating and recycled gas wherein the concentration of the vaporized substance within the gas progress to a steady state to create a substance enhanced gas; and,
   passing the substance enhanced gas from the interior of the recyclable area through the substance enhanced gaseous medium outlet.

16. The process of claim 15, wherein the step of circulating the moved gas comprises a flow rate of from about 0.01 liters/minute to about 1000 liters/minute.

17. The process of claim 15, wherein the step of passing the substance enhanced gas from the interior of the recyclable area comprises a continuous flow.

18. A delivered constant concentration vapor phase chemical substance product produced by the process of claim 15.

19. The product of claim 18, wherein the delivered constant concentration vapor phase chemical substance product comprises a substance selected from the group consisting of a calibrating, exposure or therapeutic substance.

* * * * *